(12) United States Patent
Wu

(10) Patent No.: US 10,918,655 B2
(45) Date of Patent: Feb. 16, 2021

(54) STIMULATING PLATELET GENERATION BY ACTIVATING MITOCHONDRIAL BIOGENESIS

(71) Applicant: THE GENERAL HOSPITAL CORPORATION, Boston, MA (US)

(72) Inventor: Meixiong Wu, Boston, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 70 days.

(21) Appl. No.: 16/312,709

(22) PCT Filed: Jun. 27, 2017

(86) PCT No.: PCT/US2017/039389
§ 371 (c)(1),
(2) Date: Dec. 21, 2018

(87) PCT Pub. No.: WO2018/005417
PCT Pub. Date: Jan. 4, 2018

(65) Prior Publication Data
US 2020/0030353 A1    Jan. 30, 2020

Related U.S. Application Data

(60) Provisional application No. 62/355,027, filed on Jun. 27, 2016.

(51) Int. Cl.
| *A61K 31/7056* | (2006.01) |
| *A61P 7/04* | (2006.01) |
| *A61K 31/05* | (2006.01) |
| *A61K 31/155* | (2006.01) |
| *A61K 31/195* | (2006.01) |
| *A61K 31/216* | (2006.01) |
| *A61K 31/353* | (2006.01) |
| *A61K 31/4188* | (2006.01) |
| *A61K 31/429* | (2006.01) |
| *A61K 31/4439* | (2006.01) |
| *A61K 31/498* | (2006.01) |
| *A61N 5/06* | (2006.01) |

(52) U.S. Cl.
CPC .......... *A61K 31/7056* (2013.01); *A61K 31/05* (2013.01); *A61K 31/155* (2013.01); *A61K 31/195* (2013.01); *A61K 31/216* (2013.01); *A61K 31/353* (2013.01); *A61K 31/4188* (2013.01); *A61K 31/429* (2013.01); *A61K 31/4439* (2013.01); *A61K 31/498* (2013.01); *A61N 5/062* (2013.01); *A61P 7/04* (2018.01)

(58) Field of Classification Search
CPC ... A61K 31/7056; A61K 31/05; A61K 31/155
See application file for complete search history.

(56) References Cited

U.S. PATENT DOCUMENTS

2017/0246470 A1* 8/2017 Wu ...................... A61N 5/0613

FOREIGN PATENT DOCUMENTS

| EP | 2708597 A1 | 3/2014 |
| WO | 2016/048942 A1 | 3/2016 |

OTHER PUBLICATIONS

Avery, Lindsay B., and Namandjé N. Bumpus. "Valproic acid is a novel activator of AMP-activated protein kinase and decreases liver mass, hepatic fat accumulation, and serum glucose in obese mice." Molecular pharmacology 85.1 (2014): 1-10.
Balon, Richard, et al. "The effect of lithium on platelet count." Acta Psychiatrica Scandinavica 74.5 (1986): 474-478.
Chekalina, S. I., et al. "Effect of berberine bisulfate on platelet hemostasis in thrombocytopenia patients." Gematologiia i transfuziologiia 39.5 (1994): 33-35.
Anonymous: "Drugs & Biologics Search Results", Thomson Reuters Integrity: entry No. 70019 in Drugs & Biologics: berberine chloride, Jan. 1, 2002 (Jan. 1, 2002), XP055400591, Retrieved from the Internet: URL:https://integrity.thomson-pharma.com/integrity/xmlsxl/pk_prod_list.xml_prod_listcard_pr?p_id=70019&p_tsearch=A, retrieved on Aug. 23, 2017.
Joffe, R. T., et al. "Lithium increases platelet count." The New England journal of medicine 311.10 (1984): 674-675.
PCT International Search Report and Written Opinion for corresponding International Application No. PCT/US2017/039389, dated Sep. 1, 2017, pp. 1-17.
Ramsey, Haley, Qi Zhang, and Mei X. Wu. "Mitoquinone restores platelet production in irradiation-induced thrombocytopenia." Platelets 26.5 (2015): 459-466.
Undi, Ram Babu, Usha Gutti, and Ravi Kumar Gutti. "LiCl regulates mitochondrial biogenesis during megakaryocyte development." Journal of Trace Elements in Medicine and Biology 39 (2017): 193-201.

* cited by examiner

*Primary Examiner* — Pancham Bakshi
(74) *Attorney, Agent, or Firm* — Tarolli, Sundheim, Covell & Tummino LLP

(57) ABSTRACT

A method of stimulating platelet formation using a drug that stimulates mitochondrial biogenesis is described. The drug can be used to treat a subject that has been diagnosed with thrombocytopenia or a relatively low platelet count, or it can be used to stimulate platelet generation in vitro or ex vivo. Low-level light (LLL) therapy can be used together with the drug to stimulate mitochondrial biogenesis.

9 Claims, 9 Drawing Sheets

STIMULATING PLATELET GENERATION BY ACTIVATING MITOCHONDRIAL BIOGENESIS

RELATED APPLICATIONS

Figure 1:
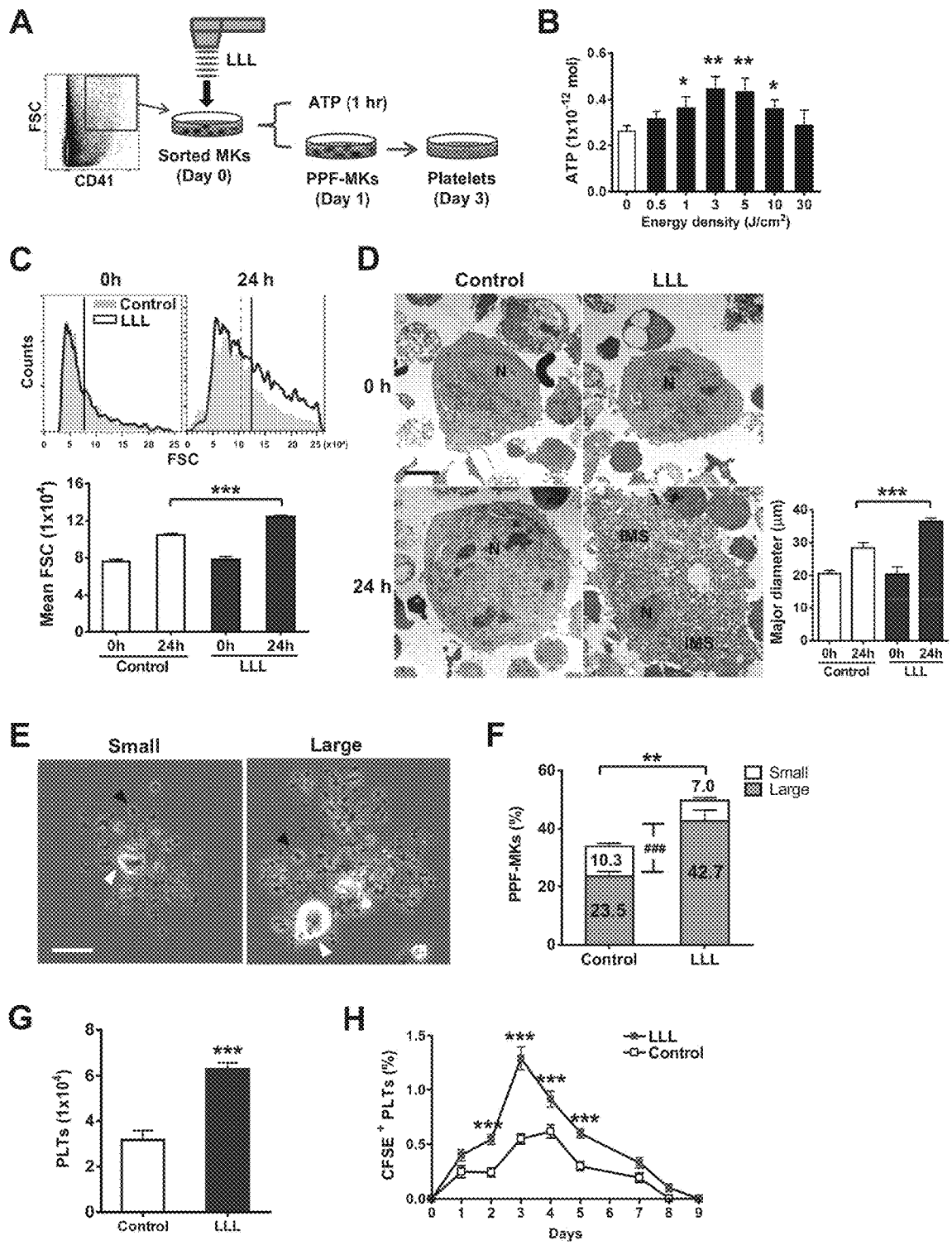

The present invention is a U.S. National Stage under 35 USC 371 patent application, claiming priority to Serial No. PCT/US2017/039389, filed on 27 Jun. 2017; which claims priority of U.S. Provisional Application No. 62/355,027, filed on 27 Jun. 2016, the entirety of which are incorporated herein by reference.

BACKGROUND

Thrombocytopenia is responsible for uncontrollable bleeding and death owing to an abnormally low number of platelets in the blood. The disease is mostly managed by platelet transfusion to date, which however is associated with a variety of complications and limited only to patients with life-threatening conditions. In the past two decades, considerable progress has been made in the development of therapeutic agents for treating thrombocytopenia and almost all of these agents augment the growth and differentiation of hematopoietic stem cells (HSCs) and/or progenitor cells for megakaryopoiesis independently on the number of circulating platelets. Hallam et al., Expert. Opin. Biol. Ther. 13, 1173-1185 (2013). Hence, a high dose of these agents cause a deleterious thrombosis, whereas a low dose exhibits modest or little effect, which severely limits their broad clinical applications. An effective modality with little risk of thrombosis remains an urgent and unmet medical need for management of thrombocytopenia.

Blood platelets are small, anucleate cells and generated from megakaryocytes (MKs) that reside primarily in the bone marrow (BM) in adult and liver and BM in newborn. The cells are differentiated from HSCs and represent the largest (50~100 μm) and also one of the rarest cells consisting of only ~0.05% of nucleated BM cells under a physiological condition, but the number of cells grow exponentially in patients suffering thrombocytopenia. During MK maturation, multiple rounds of DNA replication take place in the absence of cell division, a process called endomitosis, through which their cytoplasm is extensively enlarged and genomic DNA is amplified up to 64N in humans or 256N in mice, concurrent with synthesis of abundant cytoskeletal proteins, platelet-specific granules, and invaginated membrane systems (IMS). The cellular enlargement is followed by proplatelet formation in which the terminal mature MKs convert their entire cytoplasm into many long, branching proplatelets that are elongated at a rate of ~1 μm/min to reach the length of 250~500 um over a few hours. Patel et al., J. Clin. Invest 115, 3348-3354 (2005). The massive cytoplasm remodeling and vigorous protrusion and elongation of proplatelets are driven by microtubule forces and rely heavily on ATP generation, implicating a central role for mitochondria in the process. Consistent with this, ultrastructural abnormalities and inadequate function of MK mitochondria are commonly associated with impaired thrombopoiesis in myelodysplastic syndromes (MDS) and immune thrombocytopenia (ITP) patients. Point mutations in mitochondrial cytochrome c caused dysregulated platelet formation and thrombocytopenia specifically in humans, suggesting that platelet biogenesis is extremely sensitive to mitochondrial activity. Recent studies also showed that inadequate mitochondrial function predisposed mice lacking immediate early responsive gene X-1 (IEX-1) to thrombocytopenia upon exposure to stress. Ramsey et al., Haematologica 99, 282-291 (2014) One of the major functions of IEX-1 is to enhance ATP synthase activity at the mitochondrial respiratory chain and its null mutation compromises ATP generation and increases the production of reactive oxygen species (ROS) at mitochondria in a cell type-specific manner. The ability of mitoquinone, a mitochondrion-specific antioxidant, to completely reverse thrombocytopenia in IEX-1-deficient mice clearly suggests that mitochondrial functions are crucial in platelet generation. Ramsey et al., Platelets, 26(5):459-66 (2015).

SUMMARY

In one aspect, the present application provides a method of stimulating platelet formation in a subject by administering an effective amount of a drug that stimulates mitochondrial biogenesis to the subject. During the study of the mechanism underlying low-level light (LLL)-mediated platelet biogenesis, the inventors discovered that LLL enhanced mitochondrial biogenesis primarily in megakaryocytes, leading to increased platelet formation. Mitochondrial mass and ATP production in megakaryocytes are proportionally correlated with the level of platelet formation.

A number of mitochondrial biogenesis-promoting drugs are known. Examples include p38 mitogen-activated protein kinase activators, calmodulin-dependent protein kinase IV activators, AMP-activated kinase activators, calcineurin A activators, peroxisome proliferator response element activators, and SIRT1 activators.

In some embodiments, the subject being treated with a drug that stimulates mitochondrial biogenesis has been diagnosed with thrombocytopenia. In further embodiments, the method includes administering an anti-thrombocytopenia drug to the subject. In additional embodiments, the method includes treating the subject with low-level light (LLL) therapy. In yet further embodiments, the drug is administered together with a pharmaceutically acceptable carrier.

In another aspect, the invention provides a method of stimulating platelet formation, comprising contacting a platelet precursor with a drug that stimulates mitochondrial biogenesis. In some embodiments, the platelet precursor is a megakaryocyte or megakaryoblast. In further embodiments, the platelet precursor is in vitro or ex vivo. In other embodiments, the platelet precursor is also exposed to low-level light treatment.

BRIEF DESCRIPTIONS OF THE DRAWINGS

FIGS. 1A-1H provide graphs and images showing LLL promotes MK maturation and platelet production. (A) Illustration of time lines of ex vivo platelet differentiation from MKs. CD41+ FSC$^{high}$ MKs were sorted from BM cells, treated with or without LLL, and cultured in MK medium. MKs were collected 1 hr later for cellular ATP measurement (B), 1 day for studying proplatelet formation (C-F) or 3 days for counting platelets (G). (B) ATP was measured in $5 \times 10^4$ MKs treated with LLL at various energy densities. (C) Sizes of CD41+ MKs were analyzed by flow cytometric analysis of forward/side scatter (FSC) before and after 24 hr differentiation. (D) Representative transmission electron micrographs of MKs from at least 6 samples per group with 30 cells in each group. N, nuclear; IMS, invaginated membrane system. (E) Representative images of PPF-MKs at 24 hr post-LLL. Small, <100 μm and large, ≥100 μm in PPF-MK diameter. Filled triangles represent one of many protrusions on proplatelet shafts. Unfilled triangles indicate the nucleus. (F) The numbers indicated percentages of small or large PPF-MKs of at least 500 MKs analyzed per sample and 6 samples per group. ###P<0.001, large PPF-MKs and P<0.01, total PPF-MKs compared between the two groups. (G) The number of platelets derived from $1 \times 10^4$ MKs was estimated 3 days post-LLL on the basis of CD41 expression and FSC. (H) Sorted MKs were treated with or without LLL, labeled with CFSE, and infused into recipient mice at $1 \times 10^5$ cells per mouse. Percentages of resultant CFSE+ platelets in recipients at indicated days are shown. All data are presented as means±SEM, n=6 for B, C and G or n=10 for H; *P<0.001 compared to controls and scale bar, 5 μm for D or 25 μm for E.

FIGS. 2A-2H provide graphs and images showing the thrombopoietic effect of LLL is ATP-dependent. (A) Correlations between MK ATP levels at 1 hr post-LLL and platelets measured in 3 days later are analyzed by coefficient of determination. (B and C) Effects of LLL on platelet production (B) and ATP synthesis (C) were inhibited by 5 μg/ml inhibitor Oligomycin A (OA). (D) WT and IEX-1 KO BM cells were stained with anti-CD41 antibody and JC1. Mitochondrial membrane potential of CD41+ $FSC^{high}$ MKs was determined by flow cytometric analysis of red J-aggregate fluorescence at 590 nm. (E) Sorted MKs were treated with or without LLL, and differentiated for 1 hr before ATP measurement as FIG. 1B. (F and G) Representative images of PPF-MKs were obtained at 24 hr post-LLL from at least 6 samples per group with 25 cells in each group (F). Scale bar, 25 μm. Cell diameters were shown in G in which each symbol represents a single PPF-MK. (H) The number of platelets derived from 1×104 MKs was estimated 3 days post-LLL on the basis of CD41 expression and FSC (H). All data represent mean±SEM; n=6, P<0.01 and *P<0.001 compared between indicated groups.

FIGS. 3A-3L provide graphs and images showing that LLL stimulates mitochondrial biogenesis in polyploid MKs. (A) ATP was measured in MKs, BM cells or LSKs for indicated times post-LLL. (B & F) At 24 hr post-LLL, the indicated cells were stained with MitoTracker and analyzed by flow cytometry. (C) Mitochondrial DNA content of MKs was measured by real-time PCR and normalized with nuclear DNA. (D, G, and H) PGC-1α transcript was measured at 4 hr post-LLL (D and G), and other gene transcripts at 16 hr post-LLL by qRT-PCR (D and H). (E to I) MKs were sorted in the basis of DNA content by staining with Hoechst 33342 and FITC-anti-CD41 (E), treated with LLL or sham light, and subjected to flow cytometric analysis with MitoTracker 24 hr later (F) or RT-qPCR analysis of PGC-1α transcript 4 hr post-LLL(G), and other gene transcripts 16 hrs post-LLL (H) as above. The number of platelets derived from $1 \times 10^4$ MKs was estimated 3 days post-LLL (I). (J to L) Representative transmission electron micrographs of MKs at 24 hr post-LLL were shown in (J). Scale bar, 5 μm. The mitochondrial number of each MK (K) and the shortest distance between each mitochondrion and nearest nuclear region (L) were measured by Image J software from at least 30 MKs per group. All other data are from three independent experiments with each in triplicate and expressed as means±SEM, *P<0.05 and ***P<0.001 compared with non-LLL controls.

FIGS. 4A-4D provide graphs and images showing LLL penetrates into the bones of mice. (A) Transmittance (%) of indicated LLL modes was measured beneath mouse fresh skin and vertebral bones using a laser power meter. (B) BM cells were isolated from indicated bones in 1 hr after whole body LLL illumination at 30 J/cm² to determine ATP levels as FIG. 1B. (C and D) At 24 hr after whole body LLL illumination, the mice were i.v. injected with FITC-anti-CD41 (green) and PE-anti-CD105 (red) antibodies and sacrificed 15 min later. Fresh femurs were then removed from the mice and examined by confocal microscope (C). Arrows indicate BM MKs. Scale bar, 50 μm. Percentages of PPF-MKs were determined from at least 50 MKs per femur and 6 samples per group (D). *P<0.05, P<0.01 and *P<0.001 compared with controls or between indicated groups; and n=6 (A to C).

FIGS. 5A-5H provide graphs and images showing that LLL ameliorates thrombocytopenia induced by IR in vivo. (A) Complete blood counts of white blood cells (WBCs), lymphocytes, monocytes, granulocytes, and red blood cells (RBCs) in 3-Gy γ-irradiated mice 2 weeks after IR. Data are means±SEM (n=15). (B) Platelet counts were obtained at indicated days in 3-Gy γ-irradiated mice (IR), or IR mice treated with LLL once at 6 hours after IR (IR+1×LLL), once a day on days 0 and 1 (IR+2×LLL), or once a day from day 0 to day 3 (IR+4×LLL). Data are means±SEM (n=15). *P<0.05, P<0.01, *P<0.001 versus IR. (C) The tail bleeding time of each mouse was examined at 2 weeks after IR and presented by individual symbols. (D) Platelet volume of each mouse was examined at 2 weeks after IR. Data aremeans±SEM (n=10). (E) Representative transmission electron micrographs of platelets isolated from indicated mice at 2 weeks after IR. Scale bar, 1 mm. (F) Platelets isolated from non-IR control and IR+4×LLL mice 2 weeks after LLL were labeled with either anti-CD9 or anti-CD31 antibody, mixed, and stimulated with phorbol 12-myristate 13-acetate (100 ng/ml). Aggregated platelets indicated by double-colored events were quantified by flow cytometry and presented as mean percentages±SEM (n=6). (G) Circulating platelets and BM MKs remain within the steady-state levels in mice treated with LLL at 30 J/cm² once every other day for 12 days. Data are mean percentages±SEM of changes relative to baseline (n=6). (H) Effects of four doses of LLL on the number of MKs in γ-irradiated mice over time. Data are mean numbers±SEM of MKs per femur at indicated days (n=6). *P<0.05, ***P<0.001 compared with IRgroup. P values were determined by two-tailed Student's t test (A and H) or one-way ANOVA (B to D).

FIGS. 6A-6D provide graphs showing that LLL alleviates thrombocytopenia induced by anti-CD41 antibody or 5-FU in mice. (A and B) Mice were administered daily with 0.1 mg/kg anti-CD41 antibody over 7 days. LLL was given daily from day 3 to day 7. (C and D) Mice were injected with 50 mg/kg 5-FU on day 0. LLL was given daily for 3 consecutive days starting at 4 hr after 5-FU injection. Platelet counts (A and C) were measured daily at 6 hr post-LLL and a tail bleeding time (B and D) was examined on day 5 (B) or day 4 (D). n=6; ns, no significance; and *P<0.05, P<0.01, *P<0.001 compared between indicated groups.

FIGS. 7A-7D provide a scheme and graphs showing that LLL significantly enhances platelet generation in human MKs. (A) Illustration of the time lines of ex vivo platelet differentiation from human CD34+ cells. CD34+ cells were differentiated predominantly into MK progenitors, mature MKs, and platelets on day 6, 12, or 15, respectively. (B) ATP was measured in CD34+-derived MKs treated with LLL at various energy densities as FIG. 1B. (C) Ploidy analysis of CD34+ cultures on day 0, 6 or 12 using Hoechst 33342 staining. (D) LLL at 3 J/cm² was administered on day 0, 6, or 12 during CD34+ cell differentiation. Platelets were quantified on day 15 by flow cytometry and expressed as mean numbers±SEM of platelets derived from $1 \times 10^4$ CD34+ cells. All data are obtained from three independent experiments with each in triplicate. *P<0.05 and **P<0.01 compared with controls.

Figure 8:
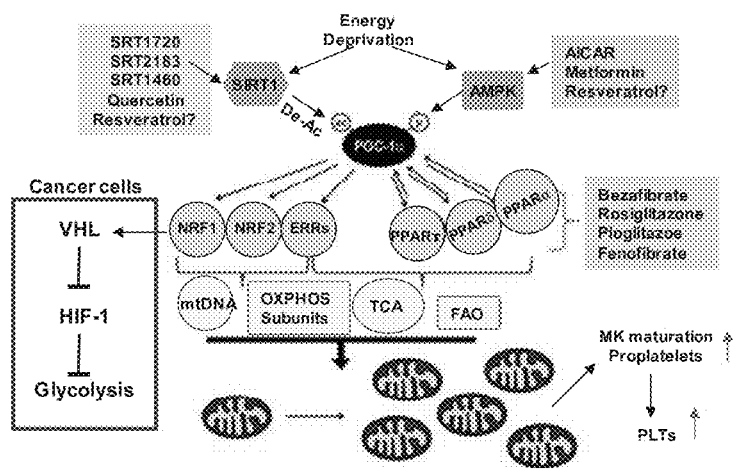

FIG. 8 provides a scheme showing the induction of PGC-1α-mediated mitochondrial biogenesis by pharmaceutical drugs. Nuclear respiratory factors (NRF-1 and NRF-2) control all ten nucleus-encoded cytochrome oxidase subunits. ERRs, estrogen-related receptors α, β, γ; TCA, Tricarboxylic acid cycle; and FAO, fatty acid oxidation.

Figure 9:
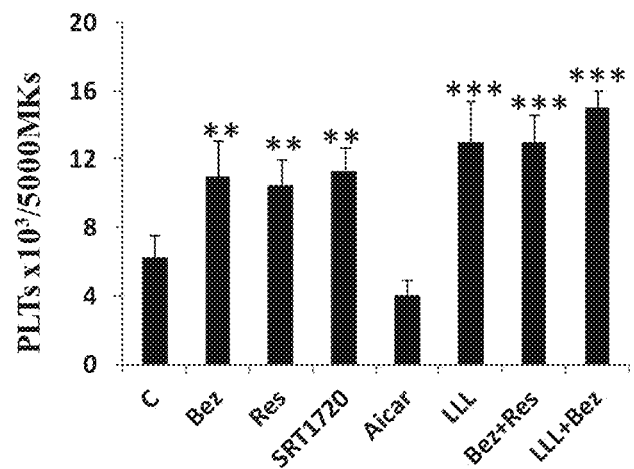

FIG. 9 provides a graph showing enhancement of platelet production ex vivo by mito-drugs. C. control; Bez, Bezafibrate (400 μM); Res, Resveratrol (50 μM); SRT1720, 0.1 μM; Aicar, AICAR (500 μM); LLL, 810 nm 3 J/cm². Mouse MKs were differentiated in MK medium for 3 days in the presence of an indicated drug or after LLLT. , p<0.01 and *, p<0.001 compared to controls. n=6.

Figure 10:
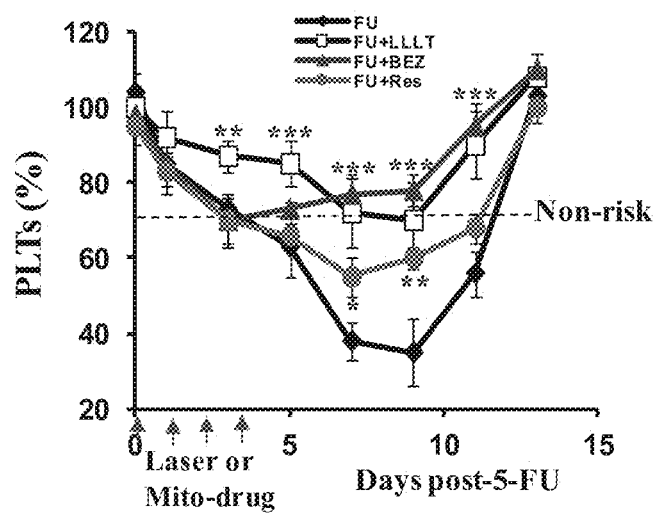

FIG. 10 provides a graph showing the enhancement of plt production by mito-drugs in vivo. All mice were treated with two doses of 5-FU (FU), along with an indicated mito-drug or LLLT for 4 consecutive days (red arrow). *, p<0.05, , p<0.01 and *, p<0.001 in the presence or absence of indicated drugs or LLLT. n=10 in each group.

Figure 11:
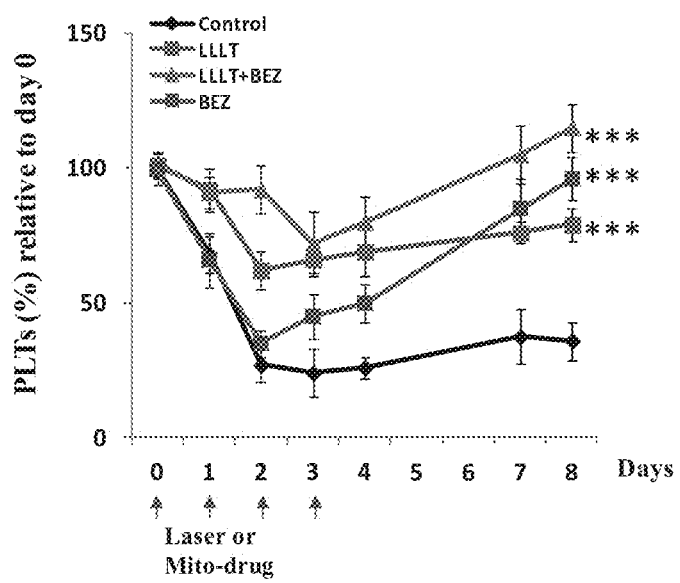

FIG. 11 provides a graph showing the enhancement of platelet production by mito-drugs plus LLLT in vivo. All mice were treated with anti-CD41 antibody daily for 7 days at 0.1 mg/kg. The mice were treated with LLLT (980 nm, 0.025 J/cm² once a day for 4 consecutive days (red arrow), BEZ twice a day each at 100 mg/kg for 4 days or both. ***, p<0.001 compared to controls. n=10 in each group.

DETAILED DESCRIPTION

The present invention provides a method of stimulating platelet formation using a drug that stimulates mitochondrial biogenesis. The drug can be used to treat a subject that has been diagnosed with thrombocytopenia or a relatively low platelet count, or it can be used to stimulate platelet generation in vitro or ex vivo. Low-level light (LLL) therapy can be used together with the drug to stimulate mitochondrial biogenesis.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "subject" can refer to any warm-blooded organism including, but not limited to, human beings, rats, mice, dogs, goats, sheep, horses, monkeys, apes, pigs, rabbits, cattle, etc. When the term is used in the context of a subject needing or requiring compositions of the present application, the term may be referred to as "a subject in need thereof" and include subjects that have been clinically diagnosed (e.g., by a medical professional, e.g., a physician) as being in need of compositions of the present application, subjects that are suspected of being in need of compositions of the present application, subjects at risk for a disease or condition and who may benefit from compositions of the present application, and subjects that are already suffering from a disease or condition and who may benefit from compositions of the present application.

The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis).

As used herein, the terms "treatment," "treating," and the like, refer to obtaining a desired pharmacologic or physiologic effect. The effect may be therapeutic in terms of a partial or complete cure for a disease or an adverse effect attributable to the disease. "Treatment," as used herein, covers any treatment of a disease in a mammal, particularly in a human, and can include inhibiting the disease or condition, i.e., arresting its development; and relieving the disease, i.e., causing regression of the disease.

As used herein, the term "preventing" includes either preventing the onset of a clinically evident disease (e.g., bleeding) altogether or preventing the onset of a preclinically evident stage of disease (e.g., thrombocytopenia) in a subject. Preventative treatment can be particularly useful in subjects identified as having an elevated risk of developing a disease. An elevated risk represents an above-average risk that a subject will develop a disease such as thrombocytopenia. Examples of factors indicating an elevated risk of developing thrombocytopenia include vitamin deficiency, leukemia, sepsis, liver failure, high rates of platelet destruction may be due to immune or non-immune conditions, treatment with a drug known to induce myelosuppression such as valproic acid or methotrexate, snakebite, radiation, radiation therapy, chemotherapy or chemo/radiation therapy in cancer patients and Lyme disease.

The term "therapeutically effective" is intended to qualify the amount of each agent which will achieve the goal of decreasing disease severity while avoiding adverse side effects such as those typically associated with alternative therapies. A therapeutically effective amount may be administered in one or more doses. Treatments that are therapeutically effective within the meaning of the term as used herein, include treatments that improve a subject's quality of life even if they do not improve the disease outcome per se.

An "Effective amount" generally means an amount which provides the desired local or systemic effect, e.g., effective to stimulate platelet formation, including achieving the specific desired effects described in this application. For example, an effective amount is an amount sufficient to effectuate a beneficial or desired clinical result.

Contacting, as used herein, refers to causing two items to become physically adjacent and in contact, or placing them in an environment where such contact will occur within a reasonably short timeframe. For example, contacting a cell with a drug that stimulates mitochondrial biogenesis includes administering the drug to a subject such that the drug will interact with cells at the sites (lung, bone marrow, spleen and liver to stimulate platelet generation. However, contacting also includes systemic administration which results in contact between the drug and platelet precursors through circulation-mediated contact.

All scientific and technical terms used in the present application have meanings commonly used in the art unless otherwise specified. The definitions provided herein are to facilitate understanding of certain terms used frequently herein and are not meant to limit the scope of the present application.

Stimulating Platelet Biogenesis

The present invention provides a method of stimulating platelet formation in a subject by administering an effective amount of a drug that stimulates mitochondrial biogenesis to the subject. A normal human platelet count ranges from 150,000 to 450,000 platelets per microliter of blood. In some embodiments, the subject is a subject in need of treatment as a result of having a low number of platelets. For example, a subjecting having about 5-15%, 15-25%, 25-35%, 35-45%, 45-55%. 55-65%, 65-75%, 75-85%, or 85-95% of normal platelet levels can be in need of treatment. Subjects having 40-95% normal platelet levels are typically not considered to have thrombocytopenia, but can still benefit from stimulation of platelet formation. Platelet concentration is measured (too small to be counted) or by placing blood in various automated Hematology Analyzers using electrical impedance or flow cytometry.

In some embodiments, the subject has been diagnosed with thrombocytopenia. Thrombocytopenia is a disorder in which a subject has an abnormally low amount of platelets, such as having below 50,000 platelets per microliter or being in the lower 2.5 percentile of the normal (average or median) platelet count for a particular human population. Thrombocytopenia usually shows no symptoms, though subjects having thrombocytopenia can sometime exhibit symptoms such as increased external bleeding such as nosebleeds or bleeding gums, bruising (purpura), and fatigue. Thrombocytopenia can be inherited, or caused as a result of a wide variety of different disorders such as sepsis or lupus, which are known to those skilled in the art.

The present invention provides a method of stimulating platelet formation. Platelets (also called thrombocytes) are a component of blood whose function (along with the coagulation factors) is to stop bleeding by clumping and clotting injured blood vessels. Platelets have no cell nucleus and are fragments of cytoplasm that are derived from megakaryocytes. On a stained blood smear, platelets appear as dark purple spots, about 20% the diameter of red blood cells. Stimulation of platelet formation refers to increasing the rate of platelet formation by megakaryocytes. Stimulation can refer to an increase of 1-10%, 10-20%, 20-30%, 30-40%, 40-50%, 50-60%, 60-70%, 70-80%, 80-90%, 90-100%, 100-150%, 150-200%, or greater than 200%.

Mitochondrial Biogenesis Stimulating Drugs

One aspect of the invention also includes administering an effective amount of a drug that stimulates mitochondrial biogenesis. The inventors have determined that mitochondria play a key role in platelet formation by platelet precursors (e.g., megakaryocytes), and that drugs that stimulate mitochondrial biogenesis can therefore be used to stimulate platelet formation. As used herein, the terms "biogenesis" refers to the synthesis of a biological substance, while the term "mitochondrial biogenesis" therefore refers to the synthesis of mitochondria. Mitochondrial biogenesis can be demonstrated by increased expression of genes associated with mitochondrial biogenesis including, but not limited to the following: PGC family members such as PGC-1α and PGC-1β, PPARδ, NRF-1, SIRT1, SIRT3, COX and AMPK; or to refer to an increased amount of mitochondrial DNA or protein content, a higher ratio of mitochondrial DNA to nuclear DNA, or an improvement in mitochondrial function such as an increase in mitochondrial enzyme activity or mitochondrial respiration. While the mitochondrial biogenesis stimulating drug can have a general stimulatory effect on mitochondrial biogenesis, the stimulation of mitochondrial biogenesis in platelet precursors such as megakaryocytes is of particular importance when it comes to stimulating platelet formation.

In some embodiments, the mitochondrial biogenesis stimulating drug is selected from the group consisting of p38 mitogen-activated protein kinase activators, calmodulin-dependent protein kinase IV activators, AMP-activated kinase activators, calcineurin A activators, peroxisome proliferator response element activators, and SIRT1 activators. These activators have all been shown to stimulate increased mitochondrial biogenesis.

In some embodiments, the mitochondrial biogenesis stimulating drug is selected from a group of specific compounds known to stimulate mitochondrial biogenesis. Examples of compounds known to stimulate mitochondrial biogenesis include interleukin 15 (U.S. Patent Pub. 2016/0354442), hydroxymethyl butyrate (U.S. Patent Pub. 2016/0346238), bioactive alkaloids (U.S. Patent Pub. 2016/0184338), rhenium-based carbon monoxide-releasing compounds (U.S. Patent Pub. 2016/0243151), muscadine and resveretrol (U.S. Patent Pub. 2013/0184228), hydroxytyrosol (U.S. Patent Pub. 2015/0030579), curcumin compounds (U.S. Patent Pub. 2015/0297536), flavonoid compounds (U.S. Patent Pub. 2014/0256741), and β2 adrenergic receptor agonists (U.S. Patent Pub. 2014/0024677). In other embodiments, the drug stimulating mitochondrial biogenesis is selected from the group consisting of bezafibrate, rosiglitazone, pioglitazoe, and fenofibrate, AICAR, metformin, resveratrol; SRT1720, SRT2183, SRT1460, and quercetin, and derivatives thereof. Derivatives, as used herein, refers to compounds having the same fundamental chemical skeletal backbone, such as a particular aromatic heterocyclic compound, in which a moiety positioned on that backbone structure is varied without losing the activity of the compound. Small variations include homologous variations such as use of different halogens, replacement of oxygen with sulfur, extension of an alkyl side chain by a single methyl group, and the like.

Candidate drugs for stimulating mitochondrial biogenesis may be tested in animal models. Typically, the animal model is one for the study of thrombocytopenia or mitochondrial biogenesis. See for example U.S. Patent Pub. 2005/0177887, which describes a PTTG knockout rodent that can be used as an animal model of thrombocytopenia. Results are typically compared between control animals treated with candidate agents and the control littermates that did not receive treatment. For example, candidate agents can be tested for their effects on PGC-1α and PGC-1β, PPARδ, NRF-1, SIRT1, SIRT3, COX and AMPK; or the amount of mitochondrial DNA or protein content, a higher ratio of mitochondrial DNA to nuclear DNA, all of which are markers of mitochondrial biogenesis. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent stimulates mitochondrial biogenesis.

Combination with an Anti-Thrombocytopenia Drug

In some embodiments, the method also includes administering a second anti-thrombocytopenia drug to the subject in combination with the drug stimulating mitochondrial biogenesis. The second anti-thrombocytopenia drug is a drug already known to be useful for treatment of thrombocytopenia. "Anti-thrombocytopenia drugs" encompass thrombopoietin (TPO), including recombinant TPO and pegylated human megakaryocyte growth and development factor (PEG-rhMGDF), and so-called TPO mimetics, which are designed to effectively treat TCP as agonists of the TPO receptor. TPO mimetic s include both nonpeptide molecules and peptides. Nplate™ (romiplostim, aka AMG 531), for example, is one of the most developed TPO mimetics and is a fusion protein of a TPO receptor-binding peptide and an Fc domain of an IgG1 antibody. Eltrombopag is an exemplary nonpeptide TPO mimetic.

Additional suitable TPO mimetics that can be used as anti-thrombocytopenia drugs are described in U.S. Pat. No. 7,160,870, e.g., 3'-{N'-[3-cyclopropyl-1-(3,4-dimethylphenyl)-5-oxo-1,5-dihydropyrazol-4-y-lidene]hydrazino}-2'-hydroxybiphenyl-3-carboxylic acid; [1-(4-fluoro-3-methylphenyl)-3-methyl-5-oxo-1,5-dihydropyrazol-4-ylidene]-hydrazino}-2'-hydroxybiphenyl-3-carboxylic acid; 3'-{N'-[3-methyl-5-oxo-1-(4-trifluoromethylphenyl)-1,5-dihydropyrazol-4-y-lidene]hydrazino}-2'-hydroxybiphenyl-3-carboxylic acid; 3-{N'-[1-(3,4-dimethylphenyl)-3-methyl-5-oxo-1,5-dihydropyrazol-4-ylidene-]hydrazino}-2-hydroxy-3'-tetrazol-5-ylbiphenyl; 3'-{N'-1-(3,4-Dimethylphenyl)-3-methyl-5-oxo-1,5-dihydropyrazol-4-ylidene-Thydrazino}-2'-hydroxybiphenyl-3-carboxylic acid; 3'-{N'-[1-(3-fluoro-4-methylphenyl)-3-methyl-5-oxo-1,5-dihydropyrazol-4-y-lidene]hydrazino}-2'-hydroxybiphenyl-3-carboxylic acid; 3'-{N'-[1-(3,4-dimethylphenyl)-3-ethyl-5-oxo-1,5-dihydropyrazol-4-ylidene-]hydrazino}-2'-hydroxybiphenyl-3-carboxylic acid; and 3-{N'-[1-(3,4-dimethylphenyl)-3-ethyl-5-oxo-1,5-dihydropyrazol-4-ylidene]-hydrazino}-2-hydroxy-3'-tetrazol-5-ylbiphenyl, and preferably 3'-{N'-[1-(3,4-Dimethylphenyl)-3-methyl-5-oxo-1,5-dihydropyrazol-4-ylidene]hydrazino}-2'-hydroxybiphenyl-3-carboxylic acid, and a pharmaceutically acceptable salt, a hydrate, a solvate, or an ester, thereof.

"Combination" refers to administration of a drug that stimulates mitochondrial biogenesis in combination with administration of an amount of an anti-thrombocytopenia drug such that there is an additive or synergistic effect, which would not be obtained if the mitochondrial biogenesis stimulating drug were administered without separate, simultaneous or sequential administration of the anti-thrombocytopenia drug. Administration of an anti-thrombocytopenia drug can be continuous, sequential or sporadic. Accordingly, a combination, as used herein, should not be limited to a single formulation comprising the inventive combination, but open to a regimen or treatment comprising the administration of active agents of the inventive combination in distinct dosage forms.

Although an appropriate dosage of drug varies depending on the administration route, age, body weight, sex, or conditions of the subject, and should be determined by the physician in the end. In the case of oral administration, the daily dosage can generally be between about 0.01 mg to about 500 mg, preferably about 0.01 mg to about 50 mg, more preferably about 0.1 mg to about 10 mg, per kg body weight. In the case of parenteral administration, the daily dosage can generally be between about 0.001 mg to about 100 mg, preferably about 0.001 mg to about 10 mg, more preferably about 0.01 mg to about 1 mg, per kg body weight. The daily dosage can be administered, for example in regimens typical of 1-4 individual administration daily. Dosage administered can also be measured by using a target serum concentration. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

Pharmaceutically Acceptable Carriers

In some embodiments, the drug stimulating mitochondrial biogenesis is administered together with a pharmaceutically acceptable carrier. Other drugs such as an anti-thrombocytopenia drug can also be administered together with a pharmaceutically acceptable carrier. The pharmaceutically acceptable carrier includes one or more additional ingredients that help administer the drug or improve its pharmacokinetics. Examples of ingredients included in a pharmaceutically acceptable carrier include pharmaceutically acceptable excipients and diluents. Suitable excipients and/or diluents are well known in the art and include pharmaceutical grade starch, mannitol, lactose, magnesium stearate, sodium saccharin, talcum, cellulose, glucose, sucrose (or other sugar), magnesium carbonate, gelatin oil, alcohol, detergents, emulsifiers or water (preferably sterile). A pharmaceutical composition including a pharmaceutically acceptable carrier may also contain preserving agents, solubilizing agents, stabilizing agents, wetting agents, emulsifiers, sweeteners, colorants, odorants, salts, buffers, coating agents or antioxidants.

A pharmaceutical composition may be adapted for administration by any appropriate route, for example by the parenteral, oral (including buccal or sublingual), rectal or topical (including buccal, sublingual, intradermal or transdermal) route. Such compositions may be prepared by any method known in the art of pharmacy, for example by admixing the active ingredient with a carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for topical administration may be formulated as ointments, creams, suspensions, lotions, powders, solutions, pastes, gels, sprays, aerosols or oils. The drugs can be delivered via the skin by microneedles or microneedle arrays: drug-laden, embedded, or coated microneedle arrays (dissolvable or non-dissolvable microneedle arrays, hollow microneedle or microneedle array. It can be also delivered by insulin-pump, catheter, wearable syringe pump and micro-delivery technologies. (the drug is unlike to be delivered by skin topical application because the drug works systemically in the body and requires a high amount). Pharmaceutical compositions adapted for rectal administration may be presented as suppositories or enemas.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

Low Level Light Therapy

In some embodiments, the method also includes treating the subject with low-level light (LLL) therapy. As used herein, the term "low level light (LLL)" can refer to a procedure that involves exposing cells (e.g., stem cells, other types of platelet precursor cells, platelets, etc.), tissue and/or at least a portion of a patient's body (e.g., platelet-making bone in adults or bone and livers in infants) to low levels of red and near infrared (NIR) light at energy densities that are low compared to other forms of laser therapy (e.g., ablation, cutting, thermal coagulation, etc.). As used herein, the term LLLT ("low level light therapy") can be used interchangeably with LLL).

Generally, low level light (LLL) can be applied (in one dose or in multiple doses) to cells (e.g., stem cells, megakaryocytes, other platelet precursor cells, platelets, etc.), tissue (e.g., bone marrow and/or liver), and/or at least a portion of a patient's body at energy densities that are low compared to other forms of laser therapy (e.g., ablation, cutting, thermal coagulation, etc.). For example, the LLL energy density can be from 0.001 J/cm$^2$ to 30 J/cm$^2$. As another example, the LLL energy density can be from 0.001 J/cm$^2$ to 20 J/cm$^2$. In a further example, the LLL energy density can be from 0.1 J/cm$^2$ to 0.5 J/cm$^2$. LLL is a simple, non-invasive, safe, convenient, and cost-effective modality that has been clinically employed for decades for pain relief and other applications. In various embodiments, the LLL used herein can have a wavelength from 600 nm to 1500 nm, a wavelength from 600 nm to 1100 nm, or a wavelength from 900 nm to 1000 nm.

While not wishing to be bound by theory, it is believed that LLL can be employed to enhance both in vivo and in vitro platelet biogenesis and to extend platelet lifespan at least because LLL can enhance ATP synthesis within cells and/or platelets. The inventors have demonstrated that mitochondria are the site where the initial effects of LLL occur. See Zhang et al., Sci Transl Med., 8(349), 349ra101 (2016), and Example I herein. LLL can excite several protein complexes (e.g., I, III, and/or IV) in the mitochondrial respiratory chain (MRC). Normally, the MRC can produce more than 90% of the ATP in the cell, but the level of ATP synthesis would be reduced in a cell under stress, so with LLL, the amount of ATP within the cell can increase. In some instances, the LLL can lead (additionally or alternatively to the increased of ATP synthesis) to enhanced oxidative phosphorylation, enhanced mitochondrial membrane potential, reduced oxidative stress, and anti-apoptosis.

Methods of Stimulating Platelet Formation

Another aspect of the invention provides a method of stimulating platelet formation that includes contacting a platelet precursor with a drug that stimulates mitochondrial biogenesis. Platelet formation can be stimulated by this method in vivo, in vitro, and ex vivo. In some embodiments, the platelet precursor is also exposed to low-level light treatment. The drug stimulating mitochondrial biogenesis can be any of the drugs described herein.

A "precursor cell" is a cell which has lost most of its multipotency to become a unipotent, partially-differentiated, cell. A "unipotent cell" used herein refers to a progenitor cell that will only differentiate into one cell type. A "platelet precursor" can refer to any cell that contributes to platelet biogenesis. These cells are commonly found within the bone marrow and/or the liver. Examples of platelet precursors include hematopoietic stem cells, promegakaryocytes, megakaryoblasts, megakaryocytes, and the like.

In some embodiments, the platelet precursor is a megakaryocyte or megakaryoblast. Megakaryocytes are large bone marrow cells with a lobulated nucleus responsible for the production of platelets. Megakaryocytes are 10 to 15 times larger than a typical red blood cell, averaging 50-100 μm in diameter. During its maturation, the megakaryocyte grows in size and replicates its DNA without cytokinesis in a process called endomitosis. The cellular enlargement is followed by proplatelet formation in which the terminal mature MKs convert their entire cytoplasm into many long, branching proplatelets that are elongated at a rate of ~1 μm/min to reach the length of 250~500 um over a few hours. This cytoplasm remodeling and vigorous protrusion and elongation of proplatelets are driven by microtubule forces and rely heavily on ATP generation by mitochondria. Thrombopoietin plays a role in inducing megakaryocytes to form proplatelets.

The following examples are for the purpose of illustration only and are not intended to limit the scope of the claims, which are appended hereto.

EXAMPLES

Example 1: Noninvasive Low-Level Laser Therapy for Thrombocytopenia

A number of investigators, including us, have shown that a special near infrared laser with a relatively low energy density, called low-level laser (LLL) or cold laser, can activate cytochrome c oxidase in the mitochondrial respiratory chain and improve mitochondrial function. Yu et al., Photochem. Photobiol. 66, 866-871 (1997); Zhang et al., J. Cereb. Blood Flow Metab 34, 1391-1401 (2014). LLL appears to be able to directly increase mitochondrial membrane potential, stimulate ATP synthesis, and modulate cellular ROS and $Ca^{2+}$ levels. Dong et al., J. Cereb. Blood Flow Metab., 35(9), 1435-44 (2015). LLL can also attenuate oxidative stress, prevent cell apoptosis, reduce inflammation, and promote cell proliferation and differentiation. AlGhamdi et al., Lasers Med. Sci. 27, 237-249 (2012). The light illumination modulates other signaling transduction pathways as well secondarily to more efficient function of mitochondria under various conditions of stress. Song et al., J. Neuroinflammation, 9, 219 (2012). Beneficial effects of LLL on traumatic brain injury have been consistently demonstrated in a number of preclinical studies. Zhang et al., J. Cereb. Blood Flow Metab, 34, 1391-1401 (2014). However, the effect of LLL on platelet generation is completely unknown.

The current study demonstrates that noninvasive whole body LLL illumination increases platelet generation and completely cures or greatly ameliorates thrombocytopenia caused by γ-irradiation, ITP or 5-fluororacil (5-FU) in mice. LLL targeted primarily MKs and bolstered mitochondrial biogenesis specifically in polyploid MKs but not in diploid cells despite the fact that LLL increased ATP production transiently in MKs, HSCs and BM cells. The finding holds great promise for LLL to be a prophylactic and therapeutic modality to manage thrombocytopenia.

Results

LLL Accelerates Proplatelet Formation and Enhances Platelet Production from MKs

To explore possible effects of LLL on platelet biogenesis, we sorted mature MKs from mouse BM cells on the basis of CD41+ and high forward scatter (FSChigh), and exposed them to 810-nm diode laser for varying durations (FIG. 1A). The sorted MKs were then cultured for 1 hr in Serum-Free Expansion Medium comprised of 100 ng/ml thrombopoietin (TPO), called MK medium hereafter, followed by ATP measurement (FIG. 1B). LLL at energy density ranging from 1 to 10 J/cm$^2$ significantly enhanced ATP synthesis in MKs, with the most prominent effect at 3~5 J/cm$^2$ (FIG. 1B). The laser at 3 J/cm$^2$ was thus selected for subsequent ex vivo studies unless otherwise indicated. We first treated the sorted MKs with LLL or sham light and cultured them in MK medium for 24 hr, followed by flow cytometric analysis of the size of 5000 MKs by FSC on the gate of CD41+ cells, which revealed a 60% increase, on average, in LLL-treated MKs, in comparison with only a 37% size increase in sham-treated MKs (p<0.001, FIG. 1C). LLL-mediated enlargement of MKs was next corroborated by transmission electron microscopy (FIG. 1D). The major diameter of the MKs was increased by 76% in the presence of LLL after 24 hr culture, as opposed to only 39% increase in the absence of LLL under similar conditions (p<0.001, FIG. 1D, lower right).

Apart from cell enlargement, LLL-treated MKs had already generated IMS throughout the entire cytoplasm after 24 hr culture (FIG. 1D, lower middle), whereas little such membrane system was formed in control MKs, suggesting that LLL accelerates MK maturation. The IMS is the membrane reservoir of proplatelets and one of the key determinants of the number of platelets generated from each MK37. In accordance with this, LLL-treated MKs produced twice as many platelets as control MKs (p<0.001, FIG. 1G), owing to an increased proportion of large proplatelet-forming MKs (PPF-MKs) (FIG. 1F). PPF-MKs were tracked in a 24 hr culture under phase contrast microscopy during which MKs converted their cytoplasm into many proplatelets that were decorated with multiple protrusions forming a "blossom"-like morphology at varying sizes (FIG. 1E). About 23.5% of CD41+ FSC$_{high}$ MKs formed large PPF-MKs with a cell diameter ≥100 µm in the absence of LLL. Strikingly, the percentage of large PPF-MKs increased to 42.7% in the presence of LLL, representing a more than 80% increase compared to sham treatment (FIG. 1F). To recapitulate this finding in vivo, mature MKs were sorted, treated with LLL or sham light, labeled with vital fluorescent dye carboxyfluorescein succinimidyl ester (CFSE), and intravenously infused into recipient mice38. LLL-treated MKs generated higher levels of platelets than control counterparts from days 2 to 5 post-infusion in recipients (p<0.001, FIG. 1H).

A Crucial Role for Mitochondrial ATP Production in Platelet Formation

Our further investigation revealed highly statistical correlations between MK ATP levels measured at 1 hr post-LLL and platelet counts measured 3 days later, with a coefficient of determination R$^2$=0.9441 (P<0.001) (FIG. 2A). LLL-mediated enhancement of platelet generation was severely blunted by inclusion of 5 µg/ml Oligomycin A (OA) in MK medium (FIG. 2B). Oligomycin A specifically inhibits mitochondrial F$_1$F$_0$-ATP synthase and reduces ATP synthesis in the cells (FIG. 2C). An importance of ATP in platelet formation is also consistent with development of irreversible thrombocytopenia upon stress in mice lacking IEX-1[39]. IEX-1 knockout (KO) MKs had reduced mitochondrial membrane potential (ΔΨ$_m$, FIG. 2D) and ATP production (p<0.01, FIG. 2E) compared with wild type (WT) controls. Proplatelet differentiation from KO MKs was severely hindered, forming a fewer and shorter proplatelet branches of much less complex network (FIG. 2F, middle panel). The average size of KO MKs was reduced by half when compared to WT MKs in 24 hr differentiation cultures (p<0.001, FIG. 2G), confirming a pivotal role of mitochondrial activity in proplatelet formation. Treatment of KO MKs with LLL elevated ATP levels by 89% (p<0.001, FIG. 2E). Remarkably, a single dose of LLL treatment substantially restored proplatelet formation of KO MKs, leading to a nearly normal PPF-MK morphology 24 hr post-LLL (FIG. 2F, right panel). The average diameter of KO PPF-MKs was only 67.0±17.8 µm, but increased to 97.6±31.3 µm following LLL treatment, representative of 46% larger of the cells (P<0.01), although they were still smaller than WT PPF-MKs (FIG. 2G). The LLL-mediated enlargement of KO PPF-MKs translated into a 2-fold increase in the number of platelets produced when compared to sham treatment in the 3-day culture (FIG. 2H). These data corroborate mitochondrial activity as a determinant factor of platelet production.

LLL Bolsters Mitochondrial Biogenesis in MKs

We next asked how brief (3 min 20 sec) LLL treatment of MKs could affect platelet differentiation days later. We first measured ATP production and observed that LLL elevated ATP production in MKs only briefly, peaking at 60 min and returning to the basal level in 90 min (FIG. 3A). This transient and robust ATP production was also evidenced in BM nucleated cells (BMs), and hematopoietic stem and progenitor cells (Lin-Scal+ cKit+ cells or LSKs) following LLL treatment (FIG. 3A). However, to our surprise, LLL-facilitated mitochondrial biogenesis occurred in MKs but not in LSKs or BMs, as indicated by doubling mitochondrial content only in MKs 24 hr post-LLL compared to controls (FIG. 3B). Mitochondrial mass was quantified by MitoTracker staining (FIG. 3B) as well as a relative ratio of mitochondrial DNA to nuclear DNA (FIG. 3C). LLL-mediated mitochondrial biogenesis was further corroborated at molecular levels. In this regard, peroxisome proliferator-activated receptor-gamma coactivator 1 alpha (PGC-1α) is a master regulatory gene for mitochondrial biogenesis and respiratory function. Greene et al., Physiol Rep. 3(7). pii: e12470 (2015). Its expression was robustly enhanced 4 hr-post LLL (FIG. 3D), after which other genes in association with mitochondrial biogenesis were also upregulated substantially in the cells (FIG. 3D). These genes included mitochondrial transcriptional factor A (Tfam), mitochondrial fission-related genes dynamin-related protein (Drp1), mitochondrial fission 1 protein (Fis1), and mitochondrial fission factor (Mff). PGC-1α expression was rather low in BM cells and LSKs and also elevated by LLL treatment, corroborating the ability of LLL to stimulate PGC-1α expression in different cell types as previously described. Nguyen et al., Mitochondrion. 14, 42-48 (2014). However, in contrast to MKs, none of Tfam, Drp1, Fis1 and Mff genes downstream of PGC-1α43 were up regulated in BMs and LSKs measured in parallel, similar to what has been described by Nguyen et al., probably owing to diploidy of the cells in contrast to the polyploidy of MKs.

To determine a crucial role for MK polyploidy in LLL-mediated biogenesis of mitochondria, we sorted CD41$^+$ MKs from BM cells on the basis of DNA content after staining with a vital fluorescent dye Hoechst 33342 (FIG. 3E). Baccini et al., Blood 98, 3274-3282 (2001). As shown in FIGS. 3F and 3G, MKs with ≥8N DNA responded to LLL much stronger than 2N/4N MKs, manifested by substantial increases in mitochondrial biogenesis and PGC-1α expression in polyploid MKs over 2N/4N MKs under similar conditions (FIG. 3F). The fraction of 2N/4N cells contained 84% of 2N MKs and 16% of 4N MKs (average=2.3N), similar to diploid cells, whereas the fraction of ≥8N cells contained 67% of 8N MKs, 28% of 16N MKs, and 5% of 32N MKs (average=11.4N), considered to be polyploid MKs. The DNA copy number-dependent effect of LLL was even more predominant in the expression of downstream genes Tfam, Drp1, Fis1 and Mff, with 100-200% increases of these downstream genes in polyploid MKs but only 0~20% increases in diploid MKs (FIG. 3H). In accordance with this, LLL raised platelet production by 200% over sham light in polyploid MKs, but only 29% in diploid MKs (FIG. 3I). These results explain that LLL enhances mitochondrial biogenesis efficiently in polyploid MKs but not in diploid cells.

The increase in mitochondrial mass was observed in multinucleated MKs as shown in FIGS. 3J and 3K where mitochondria were counted only in multi-nucleus cells before IMS was fully developed. Interestingly, apart from an increased number of mitochondria, LLL treatment also altered mitochondrial distribution in the cells. Mitochondria were more evenly distributed over the entire cells (FIG. 3J, right), whereas mitochondria in sham-treated MKs were concentrated primarily around the perinuclear region (FIG. 3J, left). Measurement of distances of individual mitochondria to the nearest nucleus revealed that 16% of mitochondria in LLL-treated MKs were located at >4 µm away from the nucleus, whereas these nucleus-away mitochondria were only 4% in control MKs (P<0.05, FIG. 3L). LLL-stimulated ATP production may promote faster movement of mitochondria, and an increased distance between any two mitochondria may send a mitochondrion-demanding signal stimulating mitochondrial fission in order to meet an energy need of specific cellular regions during MK enlargement. Mitochondrial biogenesis may warrant sufficient energy provision for MK enlargement and each platelet to inherit a few mitochondria.

LLL cures thrombocytopenia induced by γ-irradiation fast.

Figure 4:
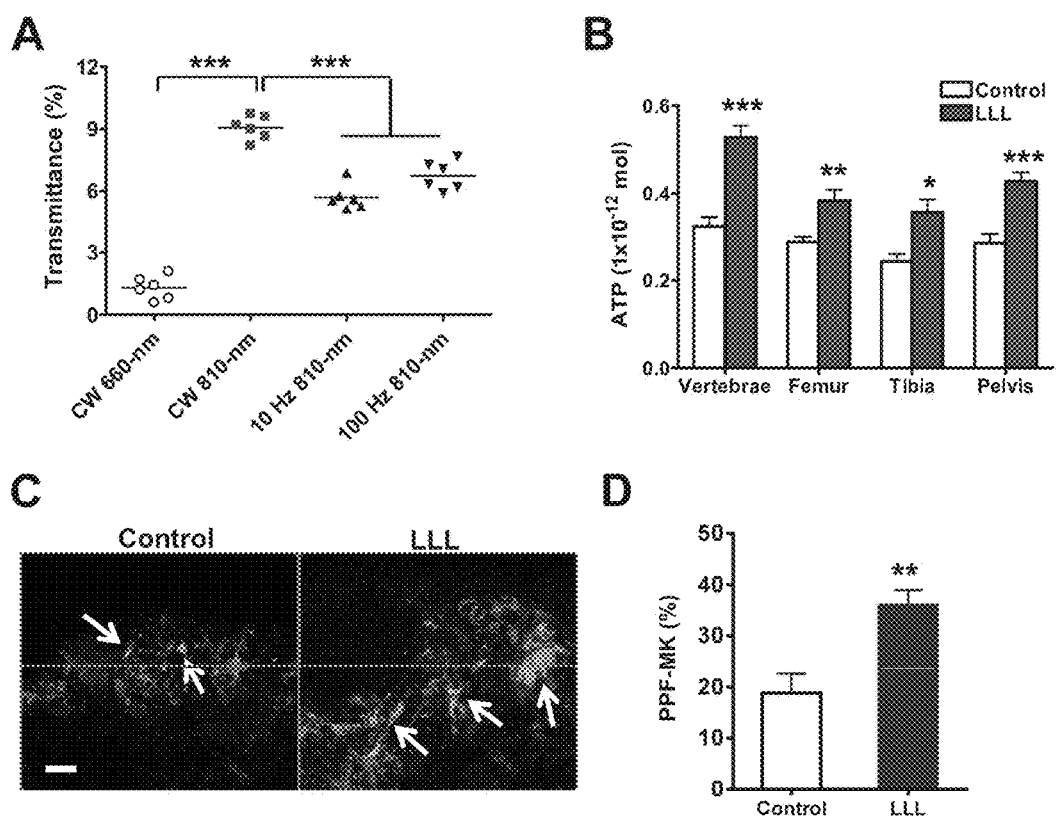

To explore a therapeutic potential of LLL, we first determined a laser dose that could sufficiently penetrate through mouse skin, muscle and bone layers, reaching the BM at 3 $J/cm^2$. Among several lasers tested, including 660-nm continuous wave laser, 810-nm 10-Hz, 100-Hz pulsed lasers, and 810-nm continuous wave laser, the latter showed most effective transmittance, with 9.0±0.6% of the laser power being transmitted into the BM (FIG. 4A). Thus, whole body illumination for 5 min with 810-nm continuous wave laser at 100 $mW/cm^2$ or a fluence of 30 $J/cm^2$ was selected so that the mouse BM cells could receive an energy density of ~3 $J/cm^2$, equivalent to the laser energy used in ex vivo culture (FIG. 1). The laser penetration was verified by increased ATP production in BM cells isolated from the vertebrae, femur, tibia, and pelvis 1 hr after whole body LLL illumination (FIG. 4B). Effect of LLL on MK differentiation in vivo was subsequently confirmed by confocal microscopy in femur bones where blood vessel and MKs were stained with PE-anti-CD105 and FITC-anti-CD41 antibodies, respectively (FIG. 4C). Large "blossom"-like MKs, likely PPF-MKs were readily seen all over the BM at 24 hr post-LLL (FIG. 4C, right panel), while such "blossom"-like cells were hardly found in the BM of control mice (FIG. 4C, left panel). Quantitatively, about 36% of MKs in LLL-treated femurs formed PPF-MKs, whereas only 19% of MKs formed PPF-MKs in control femurs (p<0.01, FIG. 4D).

The aforementioned study suggested that LLL mainly targeted MKs and thus should have greater impact in subjects with a high number of MKs like those suffering from thrombocytopenia, because the disorder triggers compensatory megakaryopoiesis. We thus induced thrombocytopenia by 3-Gy γ-irradiation (IR) (Ramsey et al., Haematologica 99, 282-291 (2014)) and then treated the mice with whole body LLL illumination for 5 min per day as defined above using the following three protocols: (1) Treated once at 6 hr post-IR (IR+1×LLL); (2) Treated twice at 6 and 24 hr post-IR (IR+2×LLL); (3) Treated 4 times for 4 consecutive days starting on day 0 (IR+4×LLL). Completed blood counts were checked weekly and compared with γ-irradiated mice receiving sham light. There were no significant alterations in the counts of white blood cells, lymphocytes, monocytes, granulocytes, or red blood cells in the presence or absence of LLL throughout the entire experimental period. However, platelet recovery was much faster in the mice in a laser dose-dependent fashion (FIG. 5A). The platelet counts reached a pre-IR level or above as early as 2 weeks (IR+4×LLL) or 3 weeks (IR+2×LLL) after IR, as opposed to 5 weeks of sham-treated mice (IR). Consistent with a rising platelet count was normalization of mouse tail bleeding time (FIG. 5B) as well as mean platelet volume in the mice when examined 2 weeks post-IR.

Figure 5:
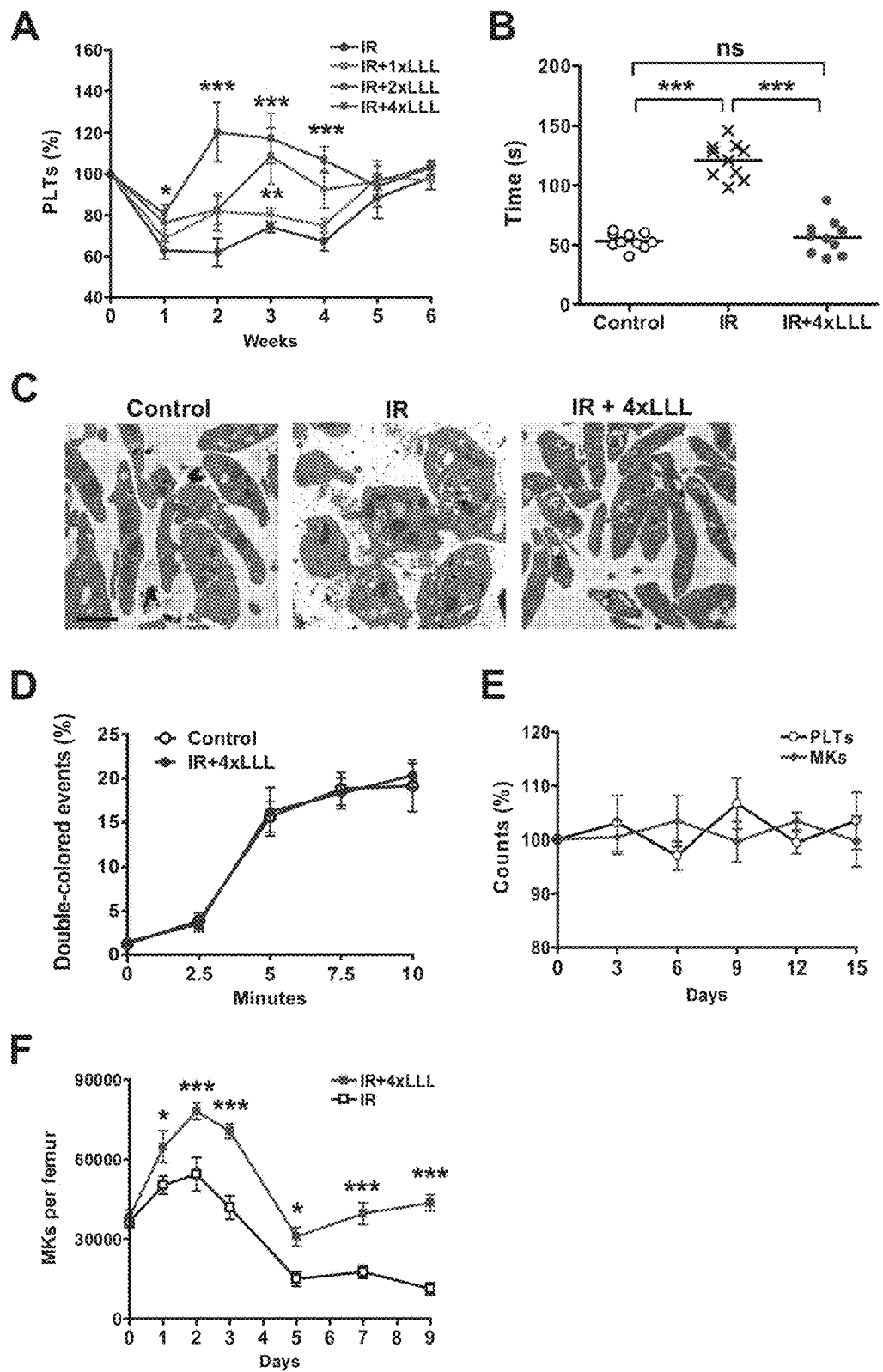

Consistent with a rising platelet count was normalization of tail bleeding time (FIG. 5C) as well as mean platelet volume (FIG. 5D) in the mice when examined 2 weeks after IR. Platelets produced in 4×LLLtreated mice were ultrastructurally indistinguishable from normal control platelets containing comparable levels of granules, mitochondria, and open canalicular systems (FIG. 5E). In contrast, platelets isolated from g-irradiated mice exhibited abnormal morphology—two to threefold bigger than a normal platelet—with lower amount of mitochondria and granules (FIG. 5E). The abnormal morphology of platelets may explain the doubled bleeding time in these mice compared to normal controls despite only a 40% drop in platelet count (FIG. 5, B and C). The overall aggregation activity of platelets isolated from 4×LLL-treated mice was also identical to that of normal controls receiving no IR (FIG. 5F). These results indicate that platelets generated by LLL treatment remained intact morphologically and functionally.

Furthermore, although LLL significantly augmented platelet production in thrombocytopenic mice, there was no significant effect on platelet counts in normal mice when LLL was administered once every other day for up to 12 days as compared to sham-treated mice (FIG. 5G). There were also no significant alterations in the number of MKs (FIG. 5G), which supports the safety of this approach, as there would be little concern about thrombosis even after repeated LLL uses.

Apart from enhancement and acceleration of proplatelet formation, LLL might also protect MKs from apoptosis induced by IR, leading to a higher number of MKs in LLL-treated versus sham-treated mice during the first 3 days after IR. The number of MKs peaked 2 days after IR and rose from 37,353 to 78,159 in one femur bone in the presence of LLL, which was about 50% higher than that in the absence of LLL (FIG. 5H). When MKs were sorted and subjected to 3-Gy IR followed by measurement of caspase-3/7 activation, a threefold increase in caspase-3/7 activity was attained, on average, in g-irradiated MKs relative to non-IR counterparts, concurrent with marked decreases in cell viability within 24 hours after IR. LLL given at 6 hours after IR significantly inhibited caspase-3 activation and enhanced cell survival of γ-irradiated MKs. LLL-mediated protection of MKs from IR-induced damage resulted in an increasing percentage of total PPF-MKs from 20.5 to 30.2%, especially the percentage of large PPF-MKs (from 5.8 to 19.2%), as well as restoration of platelet production of γ-irradiated MKs cultured ex vivo. Notably, an initial increase in the number of MKs was followed by a sharp decline to the lowest level on day 5 after IR (FIG. 5H). However, the number of MKs rose again steadily in LLL-treated mice, whereas it continued to drop in sham-treated mice (FIG. 5H), which might be attributed to better differentiation of MKs from HSCs in response to LLL, although a further study would be required to reach this conclusion.

LLL mitigates thrombocytopenia induced by anti-CD41 antibody or 5-fluorouracil.

Figure 6:
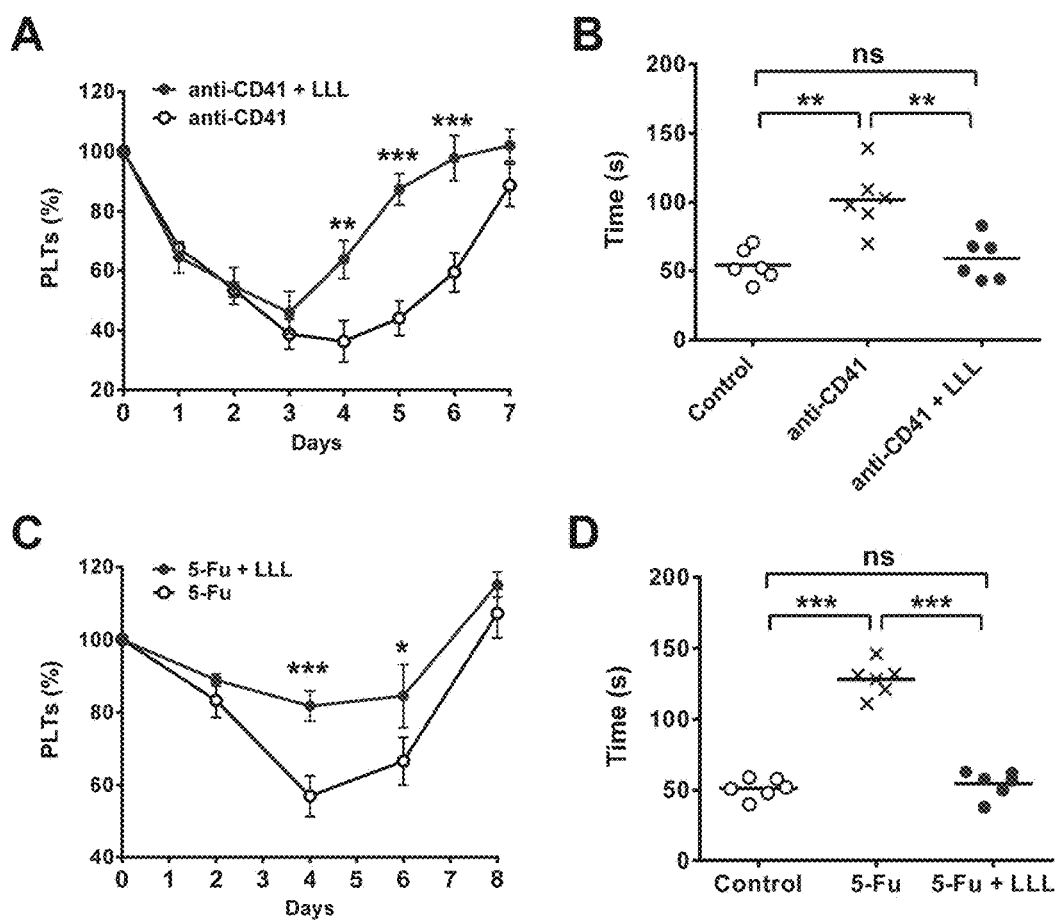

We further extended our investigation to ITP precluding that LLL-mediated thrombopoiesis was specific for thrombocytopenia induced by γ-irradiation. We depleted platelets by administering anti-CD41 antibody daily at 0.1 mg/kg body weight from day 0 to day 7 to create a commonly used animal model of ITP. Katsman et al., Transfusion 50, 1285-1294 (2010). The mice were treated with either sham light or 30 J/cm$^2$ LLL daily with an initial illumination on day 3 when platelet counts had dropped significantly, and the platelet counts were checked daily at 6 hr post-LLL (FIG. 6A). LLL lifted the nadir effectively after only two treatments (day 4) and greatly accelerated a recovery of platelet counts in the presence of anti-CD41 antibody, although platelet counts were rebound in all the mice eventually owing to compensatory thrombopoiesis (FIG. 6A). Bleeding time was also normalized on day 5 in LLL-treated animals (FIG. 6B). The ability of LLL to enhance platelet regeneration in the presence of anti-CD41 antibody greatly broadens its application as ITP is a common form of thrombocytopenia. Similar effects of LLL on platelet regeneration were also seen in mice receiving 5-FU. The chemotherapeutic drug diminished circulating platelet counts by 43% on day 4 at a dose of 150 mg/kg body weight (Chenaille et al., Blood 76, 508-515 (1990)), but 3 doses of LLL given once a day from day 0 to 2 greatly alleviated thrombocytopenia (FIG. 6C) and normalized bleeding time (FIG. 6D) in the drug-treated mice.

LLL Displays Thrombopoietic Potentials in Human Cells

Figure 7:
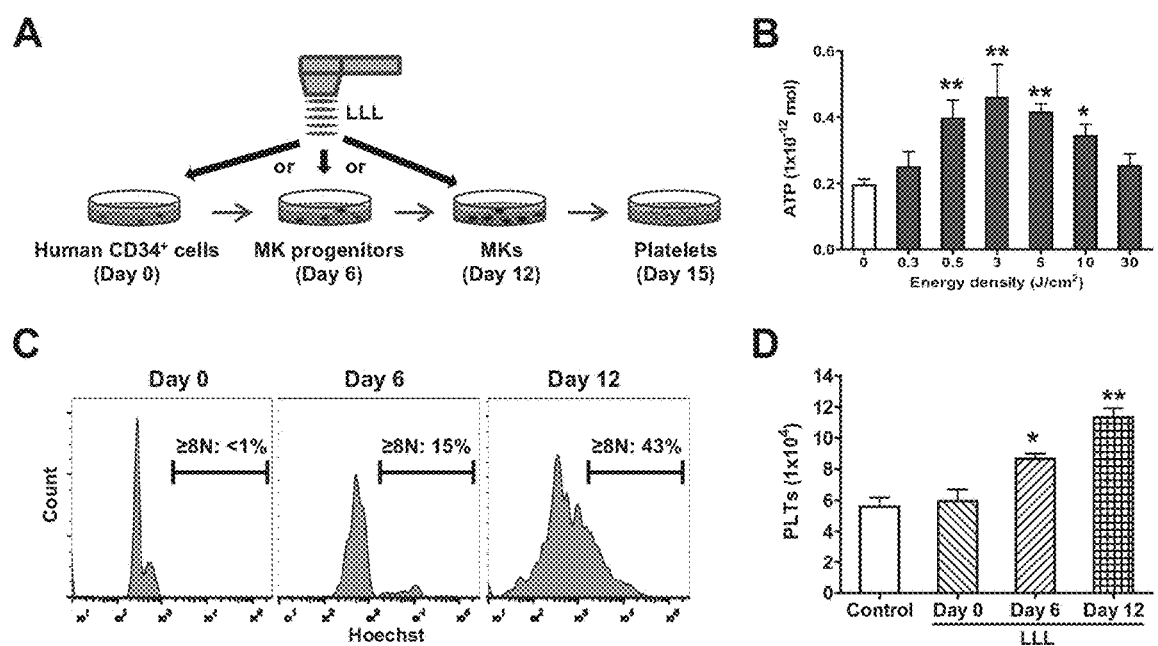

We went on to assess translational potentials of this modality using human cells. CD34+ cells were cultured in Serum-Free Expansion Medium containing 100 ng/ml human TPO, which recapitulated all the differentiation stages of megakaryopoiesis as previously described. Zeuner et al., Cancer Res. 67, 4767-4773 (2007). In the culture, CD34+ cells differentiated predominantly into MK progenitors in 6 days, MKs in 12 days and platelets in 15 days as depicted in FIG. 7A. We thus sorted mature MKs from day-12 cultures and treated the cells with LLL at various energy densities. ATP production in human MKs was significantly stimulated by LLL at energy densities ranging from 0.5 to 10 J/cm$^2$, with a peaking response at 3 J/cm$^2$ (FIG. 7B), resembling mouse MKs (FIG. 1B). So, the same laser (3 J/cm$^2$) was administered on day 0, mainly CD34+ cells in the culture, day 6 (MK progenitors) or day 12 (MKs), followed by evaluation of the platelet production on day 15. MK differentiation in these cultures was verified by an increasing polyploidy over time with a maximal percentage of polyploid cells (≥8N) on day 12 (FIG. 7C). The increases in cellular polyploidy correlated with the effect of LLL on platelet production, with the highest level of platelet production induced by LLL treatment on day 12 of the culture (FIG. 7D). The results clearly suggest that MKs are the preferential target of LLL as seen in mice and similar effects of LLL on platelet biogenesis between human and mouse MKs.

Discussion

The current investigation demonstrates that noninvasive LLL illumination can robustly increase platelet generation in thrombocytopenic mice, but not in normal controls. The laser works equally well in both human and mouse MKs ex vivo, consistent with evolutionary conservation of mitochondria and thrombopoiesis between these two species. The observation argues persuasively for the translational potential of LLL as therapeutics and prophylaxis of thrombocytopenia. The most important finding of the study is that LLL targets primarily MKs, which keeps LLL-mediated thrombopoiesis under the check of free plasma TPO that is inversely correlated with the number of circulating platelets. Shinjo et al., Leukemia 12, 295-300 (1998). In sharp contrast, all current agents used in the clinics or under the development for treating thrombocytopenia promote differentiation of MK precursors from HSCs independently on platelet counts, thereby imposing a high risk of thrombosis if employed at a high dose. As the number of MKs is reciprocally regulated by platelet counts via megakaryopoiesis, the severer thrombocytopenia, the more vigorous megakaryopoiesis would be induced, bringing about a great number of MKs, and the more prominent effect of LLL on thrombopoiesis could occur. On the contrary, LLL displays little effect on platelet counts under a physiological condition or when the platelet counts return to a normal level because of an extremely low number of MKs in these healthy subjects (FIG. 5E). In theory, LLL should benefit all patients with acquired thrombocytopenia regardless of its etiology, provided that megakaryopoiesis can be vigorously triggered by the thrombocytopenia, although IR, ITP and 5-FU-induced thrombocytopenia are tested in the current study. It is not clear however whether the modality has similar effects on inherent thrombocytopenia. For patients with insufficient megakaryopoiesis, a combination of LLL with megakaryopoietic agents such as recombinant human interleukin-11 (rHuIL-11), romiplostim and eltrombopag, may additively or synergistically augment platelet biogenesis and reduce dose-dependent side effects of these agents (Vadhan-Raj, S., Semin. Hematol., 46, S26-S32 (2009)), because these agents target early differentiation stages of platelet generation that is distinct from LLL. To date, there is no any agent, to the best of our knowledge, that specifically targets proplatelet formation or downstream of megakaryopoiesis.

The mechanism underlying LLL-mediated thrombopoiesis relies primarily on its unique effects on mitochondria. LLL protected MKs from apoptosis induced by γ-irradiation, which induces apoptosis via a mitochondrion-dependent pathway as has been demonstrated by a number of studies. Sridharan et al., Radiat. Res., 181, 324-334 (2014). Secondly, LLL specifically augmented mitochondrial biogenesis in MKs (FIG. 3), which has never been shown in other types of cells and is ascribed to a polyploidy of MKs, a unique character of MKs. Previous study had shown that near-infrared light exposure increased PGC-1α expression by about 20% in muscle cells, but expression of the downstream mitochondrial component genes (Tfam, NRF-1, Sirt3 and cytochrome c) were unaltered. Likewise, LLL increased PGC-1α transcription in BMs and LSKs, yet concomitant with no mitochondrial biogenesis (FIG. 3B) or increases in expression of other mitochondrial component genes. This unique effect of LLL on mitochondrial biogenesis in polyploid MKs is consistent with functional amplification of MK genome required for increasing synthesis of proteins in association with platelet function in parallel with cell enlargement. Raslova et al., Blood, 101, 541-544 (2003). The specific MK effect of LLL explains well why LLL affects MKs profoundly while having little impact on BMs and LSKs (FIG. 3B), lymphocytes and red blood cells under similar conditions.

Figure 2:
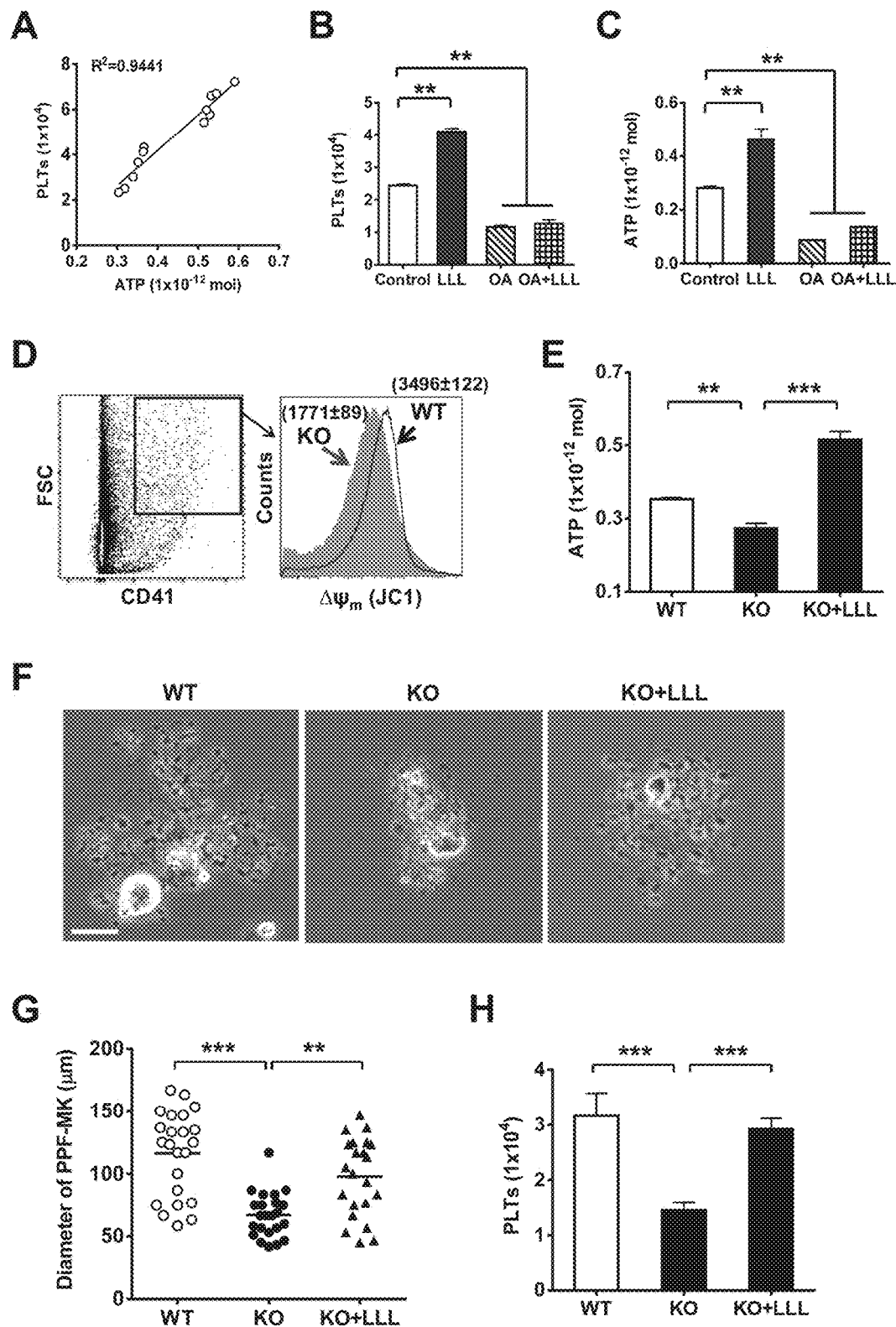
Figure 3:
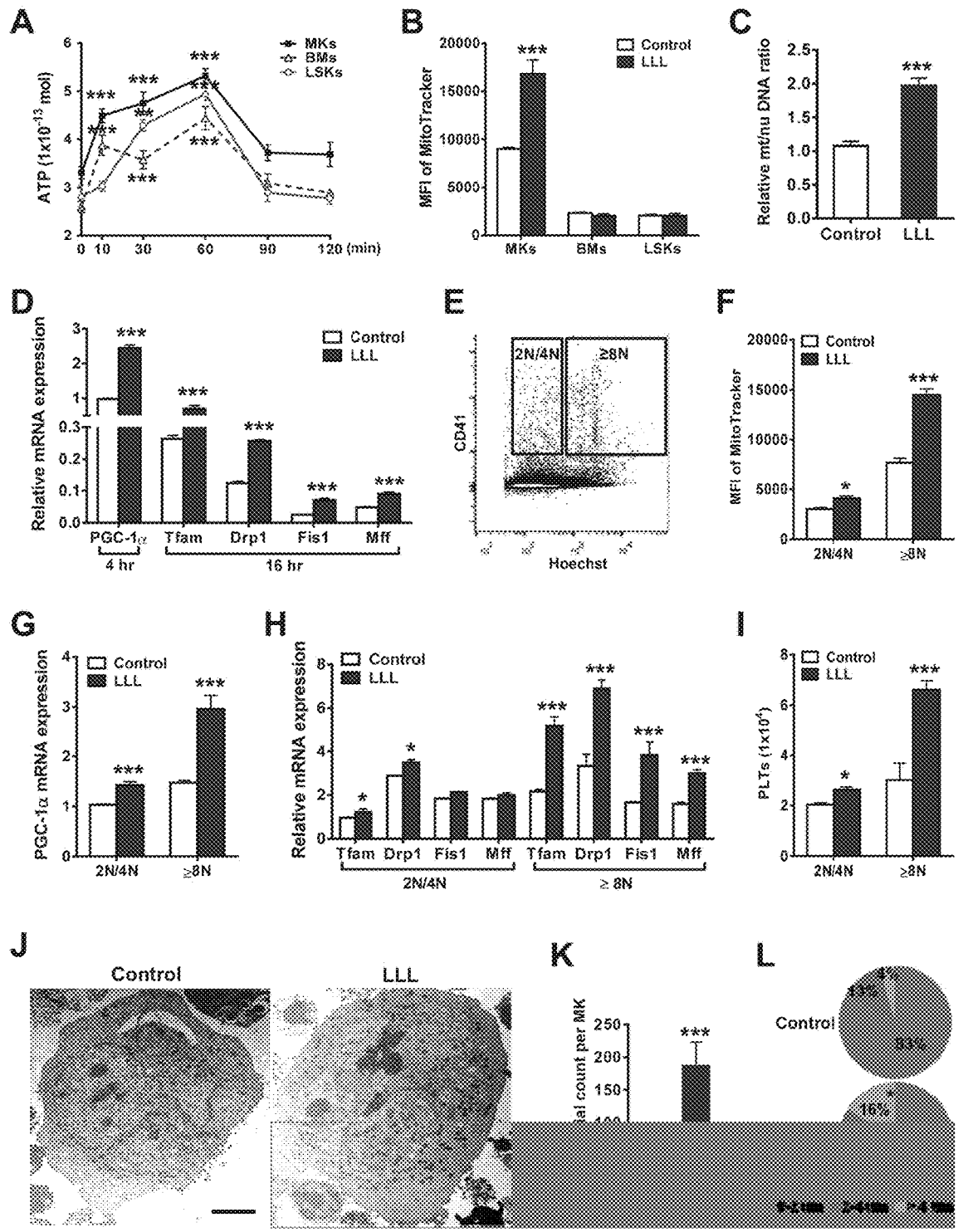

Ability of LLL to increase MK mitochondrial biogenesis and mitochondrial activity is likely to be essential in its thrombopoietic effect (Mostafa et al., Exp. Hematol. 29, 873-883 (2001)), deduced from a correlation between ATP production and platelet generation (FIG. 2A). A high energy demand of proplatelet formation is also consistent with in vivo platelet biogenesis in which MKs migrate toward BM sinusoids during proplatelet formation where oxygen levels are elevated to secure a great deal of mitochondrial oxidative phosphorylation, in contrast to HSCs and progenitor cells that reside predominantly in low-oxygen niches in the bones. Likewise, MKs tend to form proplatelets in pulmonary capillary that also contains higher levels of oxygen. In contrast, inadequate activity of mitochondria lacking IEX-1 hinders proplatelet formation, which could be normalized by LLL treatment significantly (FIG. 2). Direct evidence of ATP importance in proplatelet formation comes from the study of Richardson and Patel et al. Richardson et al., Blood 106, 4066-4075 (2005). They showed that addition of ATP to PPF-MKs permeabilized by Triton X-100 activated proplatelet elongation and significantly enhanced proplatelet growth. The study confers not only convincing evidence with respect to a rate-determinant factor of ATP in the late stage of thrombopoiesis but also a valuable hint on how to improve efficacy of platelet production both in vitro and in vivo.

LLL therapy has been routinely used in the clinics for analgesic, anti-inflammation, and wound healing for more than two decades with a long record of safety. This safe, drug-free, and donor-independent modality can be readily adopted by most practitioners as a standalone or complement treatment of thrombocytopenia. As for laser illumination in humans, super pulsed infrared lasers can penetrate tissues up to 10~13 cm without any risk of over-heating. It would be thus interesting to investigate whether the super pulsed LLL can enhance platelet biogenesis noninvasively in big animals in the near future. It is worthwhile to emphasize that this modality is not intended to replace platelet transfusions in management of bleeding, but rather, to greatly reduce the need of platelet transfusion and offer primary or secondary prophylaxis of thrombocytopenia.

Materials and Methods
Study Design

The study aimed at determining effects of LLL on platelet biogenesis and its therapeutic and prophylactic potentials for thrombocytopenia. For all ex vivo study, we used primary MKs sorted from mouse BM or CD34+ cell-derived cultures. The number of experiments (including biological and technical replicates) is defined in each figure legend. For in vivo experiments, three different mouse models were tested to validate the ability of LLL to cure or ameliorate thrombocytopenia induced by irradiation, immune depletion and 5-FU. The numbers of mice are outlined in each figure legend. Investigators were blinded to the sample identities. All outliers of study subjects were included in the data analysis.

Mice

C57BL/6 mice of either gender at 8~12 weeks of age were purchased from Jackson Laboratory. WT and IEX-1 KO mice on a 129Sv/C57BL/6 background were generated in our laboratory. Zhang et al., J. Cereb. Blood Flow Metab 34, 1391-1401 (2014). The animal protocol was approved by the subcommittee on Research Animal Care of the Massachusetts General Hospital, according to the National Institutes of Health guidelines for the Care and Use of Laboratory Animals.

Low-Level Laser Treatment

For ex vivo illumination, an infrared diode laser of 810-nm (Acculaser, PhotoThera) was set as continuous wave with a power density of 15 mW/cm$^2$ for 3 minutes and 20 seconds to obtain an energy density of 3 J/cm$^2$. For whole body LLL illumination, a hair-removed mouse was anesthetized with isoflurane and positioned under the laser lens that covered the whole trunk and limbs. The power density of LLL was 100 mW/cm$^2$, a total exposure time of 5 minutes to obtain an energy density of 30 J/cm$^2$. The first dose of LLL was given at 4-6 hr after IR or 5-FU treatment or 3 days after the first anti-CD41 antibody injection. The sham light was administered with a small soft white LED light bulb (3W, A15) from General Electric. To measure the laser power transmission, fresh skin, muscle and vertebral bone layers were removed immediately after mice were sacrificed and exposed to varying lasers. The penetrated light was measured by a laser power meter (Ophir Nova II) and a difference in light energy density on the surface of the skin and beneath the bone layer was calculated as a transmittance rate (%).

Proplatelet Formation Assays

CD41+ FSC$_{high}$ MKs were sorted, treated with or without LLL, and placed in MK medium supplemented with 3.75 g/L methylcellulose (Sigma). The cells were differentiated in a chamber with 5% $CO_2$ at 37° C. Phase contrast live cell images were recorded up to 24 hr by a time-lapse microscope (Zeiss Axio Observer Z1) using a 40× objective. The longest or major diameter of PPF-MK was measured by AxioVision software (Zeiss). PPF-MKs with a diameter <100 μm were defined as "small", and a diameter ≥100 μm as "large". To estimate a ratio of PPF-MK formation, 500 CD41+ FSC$_{high}$ MKs were plated in each well, and the percentage of PPF-MKs was manually calculated from at least 6 samples per group by an investigator blinded to the treatment.

Tracking Femur MKs

At 24 hr after whole body LLL illumination, FITC-anti-CD41 and PE-anti-CD105 antibodies (BioLegend) each at 12 μg per mouse were intravenously administered. The mice were sacrificed 15 min later and the femurs were removed and examined by confocal microscopy. At least 50 MKs were tracked in 6 views randomly selected from each femur and the percentages of PPF-MKs were calculated from 6 samples per group in a sample-blind manner.

Human Megakaryocyte and Platelet Cultures

Frozen human BM CD34+ cells were obtained from STEMCELL Technologies and differentiated in Serum-Free Expansion Medium supplemented with 100 ng/ml human TPO (STEMCELL Technologies) as previously described. Zeuner et al., Cancer Res. 67, 4767-4773 (2007). During the culture, megakaryocytic differentiation stages were routinely evaluated by May-Grünwald-Giemsa staining (Sigma) and CD41 levels via flow cytometry. CD34+ cells, MK progenitors, mature MKs or platelets were collected on 0, 6, 12, or 15 days of the culture, respectively.

Statistical Analysis

Results are presented as means±SEM. Statistical significance was assessed with 2-tailed student's t-test for comparison between two groups or one way ANOVA for multiple group comparison. A value of p<0.05 was considered statistically significant. The relationship between ATP level and platelets was tested by regression and correlation analysis, and coefficient of determination ($R^2$) was calculated. All statistical analyses were performed using GraphPad Prism 6.0 (GraphPad Software).

Example 2: Mitochondrial Biogenesis-Promoting Drugs for Platelet Regeneration

Mitochondrial biogenesis has been extensively investigated for decades, primarily in tissues that have a high-energy demand such as heart, liver, skeletal muscle, fat, and brain. Although megakaryocytes (MKs) are also abundant in mitochondria during final differentiation stages, an importance of mitochondrial biogenesis in platelet biogenesis has not been appreciated until our recent studies. Yang et al., Sci. Rep. 6:38238 (2016); Zhang et al., Sci. Transl. Med., 8:349ra101 (2016). We demonstrated that the massive cytoplasm remodeling and vigorous protrusion and elongation of proplatelets in the final stage of platelet formation rely heavily on mitochondrial activity. In support, point mutations of mitochondrial cytochrome c caused dysregulated platelet formation and thrombocytopenia in humans, concurrent with no other disorders in the family. Morison et al., Nat. Genet., 40:387-389 (2008). We also showed that inadequate mitochondrial function predisposed to thrombocytopenia upon stress in mice. Ramsey et al., Haematologica 99:282-291 (2014). On the contrary, low-level laser therapy (LLLT) bolstered mitochondrial biogenesis in MKs and platelet formation and mitigated thrombocytopenia in several murine models. These findings raise an intriguing possibility that mitochondrial biogenesis-promoting drugs, collectively called here mito-drugs, may be able to augment platelet regeneration and treat thrombocytopenia.

Mitochondrial biogenesis can be pharmacologically manipulated by inducing the expression of peroxisome proliferator-activated receptor (PPAR)-gamma coactivator 1 alpha (PGC-1α), a master regulatory gene for mitochondrial biogenesis as depicted in FIG. 8. Scarpulla, R. C., Biochim. Biophys. Acta 1813:1269-1278 (2011). The gene can be transcriptionally activated by various kinases and PPAR agonists or post-translationally modified via phosphorylation with AMP-activated kinase (AMPK) and deacetylation (De-Ac) with silent information regulator two protein 1 (SIRT1) (FIG. 8). Komen et al., Br. J. Pharmacol. 171: 1818-1836 (2014). A number of studies have shown that mitochondrial biogenesis can be sufficiently induced by pan-PPAR agonists including bezafibrate (BEZ), rosiglitazone, pioglitazoe, and fenofibrate; activators for AMPK like AICAR (AMP mimetic), metformin, and maybe resveratrol; and activators for SIRT1 such as SRT1720, its derivatives SRT2183 and SRT1460, quercetin, and perhaps resveratrol. Uittenbogaard, M. and Chiaramello, A., Curr. Pharm. Des, 20:5574-5593 (2014); Arbel et al., Cardiovasc. Diabetol., 15:11 (2016). Some of these mito-drugs are currently in clinical trials for treating metabolic syndrome, obesity, Duchenne muscular dystrophy and various neurodegeneration diseases, while others like BEZ, metformin are already in clinics for decades. Hofer et al., Hum. Mol. Genet. 23:2400-2415 (2014). However, none of these drugs have ever been investigated for their ability, either alone or in any combination, to enhance mitochondrial biogenesis in MKs or platelet production.

Some mito-drugs tested enhance platelet production from MKs ex vivo. We found that resveratrol (Res), BEZ, and SRT1720, but not AICAR, could enhance platelet generation from MKs ex vivo significantly, albeit at a slightly lesser extent than LLLT (FIG. 9). The concentration used for individual drugs is the one commonly used for inducing PGC-1α expression in other cell cultures except for SRT1720 that was used at a 100× lower concentration. A higher concentration of SRT1720 did not increase platelet production significantly. Perhaps, the concentration of each drug can be further optimized for enhancing platelet production. These mito-drugs also exhibit benefits to chemotherapy (Aires et al., Mol. Nutr. Food Res. 58:1785-1794 (2014); Liu et al., J. Cancer 6:1214-1221, (2015); Fresco et al., Curr. Pharm. Des 16:114-134 (2010)), and may thus confer duo benefits to cancer patients receiving chemotherapy, although further studies are required to conclude it.

Mito-drugs augment platelet production similarly as LLLT in vivo, though in a delay: To demonstrate mito-drugs-mediated platelet biogenesis in vivo, B6 mice at 8 wks of age were given two doses of chemo-drug 5-fluorouracil (5-FU): 120 and 90 mg/kg body weight on days 1 and 4, respectively, to induce thrombocytopenia (FIG. 9). The 5-FU-treated mice were gavaged with BEZ or Res at 100 mg/kg body weight or vehicle control twice a day for 4 consecutive days starting at 6 hr after the first 5-FU injection. For comparison, 5-FU-treated mice were also administered LLL daily for 4 consecutive days in parallel. BEZ exhibited a similar efficacy as LLLT in retaining plt counts on and after day 7, but it was inferior to LLLT prior to day 7, probably because LLLT protected MKs and platelets from apoptosis but BEZ did not. In spite of a delay relative to LLLT, BEZ was able to sustain platelet counts at or above a non-risk level of platelet counts (70% the normal value) and lessened the nadir substantially, which is the key as the nadir imposes the riskiest of bleeding. Res also augmented platelet biogenesis and lifted the nadir significantly but its efficacy was relatively weak compared to BEZ or LLLT. The results confirm that induction of mitochondrial biogenesis can mitigate thrombocytepenia. The dosage of Res or BEZ in the study is comparable to the current dosage of the mito-drug in the clinics. Whether or not a higher dose or dosage of BEZ can further increase the efficacy remains to be investigated.

A combination of LLLT and mitochondrial drugs can extend the benefit. A quick effect of LLLT and convenience of oral BEZ promoted us to combine the two in treatment of thrombocytopenia induced by anti-CD41 antibody, a commonly used model of immune thrombocytopenia (ITP). Anti-platelet antibody was given daily from days 0 to 7, which caused a precipitous decline of the circulating platelets after two injections and reached a nadir on day 2. The platelet level remained below 40% the normal platelet counts throughout 8 days of experiment. BEZ alone did not effectively prevent platelet counts from dropping to the nadir, but it raised platelet counts significantly soon after the nadir. In marked contrast, LLLT sustained the level of platelet counts above 50% the normal levels, greatly diminishing the risk of bleeding. A combination of BEZ and LLLT further improved platelet regeneration and sustained platelet counts at or above 70% the normal level, which is a safe level of circulating platelet counts. These results demonstrate potentials of mito-drugs, either alone or in combination with LLLT or other megakaryopoiesis-promoting drugs to treat thrombocytopenia. These results are shown in FIGS. 10 and 11.

The complete disclosure of all patents, patent applications, and publications, and electronically available materials cited herein are incorporated by reference. Any disagreement between material incorporated by reference and the specification is resolved in favor of the specification. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of stimulating platelet formation in a subject by administering an effective amount of a drug that stimulates mitochondrial biogenesis to the subject, wherein the mitochondrial biogenesis stimulating drug is selected from the group consisting of bezafibrate, rosiglitazone, pioglitazone, fenofibrate, 5-aminoimidazole-4-carboxyamide-1-beta-D-ribofuranoside (AICAR), metformin, resveratrol, SRT1720, SRT2183, SRT1460, and quercetin.

2. The method of claim 1, wherein the subject has been diagnosed with thrombocytopenia.

3. The method of claim 2, further comprising administering an anti-thrombocyotpenia drug to the subject.

4. The method of claim 1, further comprising treating the subject with low-level light (LLL) therapy.

5. The method of claim 1, wherein the drug is administered together with a pharmaceutically acceptable carrier.

6. A method of stimulating platelet formation, comprising contacting a platelet precursor with a drug that stimulates mitochondrial biogenesis, wherein the mitochondrial biogenesis stimulating drug is selected from the group consisting of bezafibrate, rosiglitazone, pioglitazone, fenofibrate, 5-aminoimidazole-4-carboxyamide-1-beta-D-ribofuranoside (AICAR), metformin, resveratrol, SRT1720, SRT2183, SRT1460, and quercetin.

7. The method of claim 6, wherein the platelet precursor is a megakaryocyte or megakaryoblast.

8. The method of claim 6, wherein the platelet precursor is also exposed to low-level light treatment.

9. The method of claim 6, wherein the platelet precursor is in vitro or ex vivo.

* * * * *